United States Patent [19]

Umemura et al.

[11] 4,267,385
[45] May 12, 1981

[54] PROCESS FOR THE CATALYTIC PREPARATION OF ACROLEIN AND METHACROLEIN

[75] Inventors: Sumio Umemura; Kyoji Ohdan; Hiroyuki Asada, all of Ube, Japan

[73] Assignee: UBE Industries, Ltd., Yamaguchi, Japan

[21] Appl. No.: 102,992

[22] Filed: Dec. 12, 1979

[30] Foreign Application Priority Data

Dec. 27, 1978 [JP] Japan .................................. 53/160109

[51] Int. Cl.³ .............................................. C07C 45/35
[52] U.S. Cl. .................................... 568/479; 568/476; 252/466 J; 252/454
[58] Field of Search .................... 260/604 R; 568/479, 568/476; 252/466 J, 454

[56] References Cited

U.S. PATENT DOCUMENTS

| | | | |
|---|---|---|---|
| 3,198,751 | 8/1965 | Bethall et al. .......................... | 252/461 |
| 3,522,299 | 7/1970 | Takenaka et al. ................ | 260/604 R |
| 3,686,138 | 8/1972 | Yoshino ................................. | 252/456 |
| 3,686,295 | 8/1972 | Grasselli et al. ................. | 260/604 R |
| 3,825,502 | 7/1974 | Takenaka et al. ................ | 260/604 R |
| 3,936,505 | 2/1976 | Oda et al. .......................... | 260/604 R |
| 4,171,328 | 10/1979 | Umemura et al. ................ | 260/604 R |

FOREIGN PATENT DOCUMENTS

| | | |
|---|---|---|
| 18-68762 | 3/1943 | Japan . |
| 45-8206 | 3/1970 | Japan . |
| 48-1645 | 1/1973 | Japan . |
| 51-40957 | 10/1976 | Japan . |
| 51-47684 | 12/1976 | Japan . |
| 52-22359 | 6/1977 | Japan . |
| 52-50766 | 12/1977 | Japan . |
| 1290198 | 8/1969 | United Kingdom . |

Primary Examiner—Werren B. Lone
Attorney, Agent, or Firm—Burgess, Ryan and Wayne

[57] ABSTRACT

Acrolein or methacrolein is produced in a high percent of yield by a catalytic oxidation of propylene or isobutylene in the presence of a catalyst of the empirical formula:

$$Mo_{10}Co_{0\sim10}Ni_{0\sim10}Fe_{0.1\sim5}Bi_{0.001\sim3}Al_{0.05\sim10}Ti_{1\sim15}A_{0\sim4}O_{33.2\sim99}$$

wherein A denotes at least one alkali metal atom and the sum of the numbers of cobalt atoms and the nickel atoms is 1 to 10 per 10 atoms of molybdenum, which catalyst has an excellent crushing strength and exhibits a high catalyst activity.

11 Claims, No Drawings

PROCESS FOR THE CATALYTIC PREPARATION OF ACROLEIN AND METHACROLEIN

FIELD OF THE INVENTION

The present invention relates to a process for the catalytic preparation of acrolein and methacrolein. More particularly, the present invention relates to a process for the preparation of acrolein or methacrolein, in a high percent of yield and a high space time yield thereof, by means of a catalytic oxidation of propylene or isobutylene, at an elevated temperature, in the presence of a Mo-Co and/or Ni-Bi-Fe-Al-Ti-O type catalyst.

BACKGROUND OF THE INVENTION

It is known that unsaturated aliphatic aldehyde, for example, acrolein or methacrolein, can be produced by various methods of catalytic oxidation of olefins, for example, propylene or isobutylene, in gas phase with molecular oxygen, at an elevated temperature, in the presence of various types of catalysts. For example, U.S. Pat. No. 3,522,299 discloses a method for producing acrolein in the presence of a Mo-Bi-Fe-Co-O type catalyst. This method results in the production of acrolein in a poor yield of 71.5% or less. Japanese Patent Application Publication (Kokoku) No. 52-50766 discloses a method for producing acrolein in the presence of an aluminum-containing Mo-Co-Bi-Fe-Al-O type catalyst. However, this method results in a poor yield of acrolein of 81% or less. The above-mentioned yields of acrolein are unsatisfactory for the industrial production of acrolein.

Also, various methods for producing the unsaturated aliphatic aldehydes in the presence of various types of catalysts containing titanium as a catalyst component, are disclosed in U.S. Pat. No. 3,198,751 (Sb-Ti-O type catalyst), Japanese Patent Application Publication (Kokoku) No. 43-6762 (Ti-Te-O type catalyst), Japanese Patent Application Publication (Kokoku) No. 45-8206 (W-Ti-P-Te-Ca-O type catalyst), British Pat. No. 1290198 (Ti-Fe-Ni-Bi-Mo-O type catalyst, U.S. Pat. No. 3,686,138 (Sb-Si-Ti-O type catalyst), Japanese Patent Application Publication (Kokoku) No. 47-40957 (Ti-SB-Te-Si-O type catalyst), Japanese Patent Application Publication No. 48-1645 (Ni-Co-Fe-Bi-Ti-K-Mo-O type catalyst), Japanese Patent Application Publication (Kokoku) No. 51-47684 (Ni-Co-Fe-Bi-Ti-K-Mo-O type catalyst), Japanese Patent Application Publication No. 52-22359 (Mo-Bi-Ti-O type catalyst), U.S. Pat. No. 3,872,148 (Mo-Bi-W-Ti-O type catalyst) and U.S. Pat. No. 3,936,505 (Mo-Nb-Ti-O type catalyst). However, the above-mentioned titanium containing catalysts still result in a poor yield of the unsaturated aliphatic aldehydes, for instance, acrolein or methacrolein, of, at the highest, slightly more than 80%. This yield is not satisfactory for the industrial production of unsaturated aliphatic aldehydes. That is, both the conventional aluminium-containing catalysts and the conventional titanium-containing catalysts fail to convert the olefins into the unsaturated aliphatic aldehydes in a satisfactorily high yield thereof.

With respect to the conventional processes for the preparation of acrolein or methacrolein by the catalytic oxidation of propylene or isobutylene with molecular oxygen, at an elevated temperature, it is known that it is extremely difficult to increase the percent of yield of acrolein or methacrolein while maintaining the percent of selectivity to acrolein or methacrolein at a high level. Usually, when the conventional catalysts are used, the production of acrolein or methacrolein while maintaining the percent of conversion of propylene or isobutylene at a high level, results in a poor percent of selectivity to acrolein or methacrolein. This poor percent of selectivity causes the percent of yield of acrolein or methacrolein to be poor. Also, in order to produce acrolein or methacrolein in a high percent of selectivity thereto, it is necessary to maintain the percent of conversion of propylene or isobutylene at a low level. However, this low level of the percent of conversion results in a poor yield of acrolein or methacrolein.

In the industrial production of acrolein or methacrolein, it is required that the catalyst exhibit a high strength to crushing during the reaction. However, with respect to the conventional types of catalysts, it is known that the increase in the crushing strength of the catalysts results in a decrease in the percent of conversion having high crushing strengths cause the percent of yield of acrolein or methacrolein to be poor.

It is also known that the conventional types of catalysts can not produce acrolein or methacrolein at a satisfactory high level of space time yield (g/l·hr) thereof. The term "space time yield" refers to an amount (g) of the produced acrolein or methacrolein per unit time (hr) and unit amount in volume (l) of the catalyst used.

Japanese Patent Application Publication (Kokoku) No. 52-50766, (the Applications corresponding to those in the present application) discloses a Mo-Co-Bi-Fe-Al-O type catalyst containing aluminum as a catalyst component. This type of catalyst is effective for producing acrolein or methacrolein in a considerable high yield thereof. However, it is desired that this type of catalyst be further improved so as to increase the percent of yield, the space time yield and the crushing strength of the catalyst.

SUMMARY OF THE INVENTION

An object of the present invention is to provide a process for the catalytic preparation of acrolein or methacrolein in an excellent high percent of yield thereof.

Another object of the present invention is to provide a process for the catalytic preparation of acrolein or methacrolein in an excellent high space time yield thereof.

Still another object of the present invention is to provide a process for the catalytic preparation of acrolein or methacrolein by using a catalyst having an excellent high crushing strength.

The above-mentioned objects can be attained by the process of the present invention, which comprises bringing, at an elevated temperature, a reaction feed containing propylene or isobutylene and molecular oxygen each in gas phase, into contact with a catalyst consisting essentially of an oxide composition of the empirical formula:

$$Mo_aCo_bNi_cFe_dBi_eAl_fTi_gA_hO_i$$

wherein A represents at least one alkali metal atom; the subscripts a, b, c, d, e, f, g and h respectively denote the numbers of the respective atoms of the elements, the ratio a:b:c:d:e:f:g:h being in a range of 10:0 to 10:0 to 10:0.1 to 5:0.001 to 3:0.05 to 10:1 to 15:0 to 4 and the ratio a:(b+c) being in a range of 10:1 to 10, and; the subscript i represents the number of oxygen atoms which satisfies the average valency of the elements, the ratio a:i being in a range of 10:33.2 to 99.

The process of the present invention is characterized by using the new type of catalyst as specified above. This catalyst is characterized by containing both aluminium and titanium, as catalyst components, in addition to molybdenum, cobalt and/or nickel, bismuth, iron and optionally, alkali metal, and the atomic ratio of the elements is in the above-specified range. This type of catalyst exhibits an excellent crushing strength and allows the process of the present invention to produce acrolein or methacrolein in a very high percent of yield and an excellent space time yield thereof. Also, the alkali metal which is an optional catalyst component is effective for increasing the percent of yield of acrolein or methacrolein.

DETAILED EXPLANATION OF THE INVENTION

In the process of the present invention, a reaction feed containing propylene or isobutylene and molecular oxygen, each in gas phase, is brought into contact with a catalyst, at elevated temperature. The catalyst consists essentially of an oxide composition of the empirical formula:

$$Mo_aCo_bNi_cFe_dBi_eAl_fTi_gA_hO_i$$

wherein A represents at least one alkali metal atom; the subscripts a through h respectively respresent the number of atoms of the respective elements, and the subscript i respresents the number of oxygen atoms which satisfies the average valency of the elements.

When the subscript a represents a number 10, the subscripts b through i respectively represent the following numbers.

b=0 to 10
c=0 to 10
b+c=1 to 10, preferably, 4 to 9
d=0.1 to 5, preferably, 1 to 3
e=0.001 to 3, preferably, 0.05 to 2
f=0.05 to 10, preferably, 1 to 5
g=1 to 15, preferably, 3 to 10
h=0 to 4, preferably, 0.005 to 0.5
i=33.2 to 99.

In the oxide composition of the above-mentioned empirical formula, it is important that titanium be used in an amount of from 1 to 15 atoms, preferably, 3 to 10 atoms, per 10 molybdenum atoms. When the amount of titanium is less than 1 atom per 10 molybdenum atoms, the objects of the present invention will not be attained. Also, when the amount of titanium is more than 15 atoms per 10 molybdenum atoms, the resultant catalyst will cause the percent of conversion of propylene or isobutylene to be substantially decreased, while the resultant catalyst will exhibit a satisfactory crushing strength. The decrease in the percent of conversion will result in a decrease in the percent of yield of acrolein or methacrolein.

The catalyst of the above-mentioned empirical formula, contains either one of or both cobalt and nickel, as catalystic components. However, a catalyst containing cobalt and no nickel or both cobalt and nickel is preferred, rather than a catalyst containing nickel and no cobalt, because the former catalyst causes the resultant catalyst to exhibit a slightly higher percent of yield of acrolein or methacrolein than that of the latter catalyst.

The catalyst may contain the alkali metal as an optional catalytic component. The alkali metal component results in a catalyst which causes the percent of yield of acrolein or methacrolein to remarkably increase. The alkali metal may be selected from the group consisting of lithium, sodium, potassium, rubidium, cesium and francium. The above-mentioned alkali metals exhibit a similar catalytic effect to each other. However, since francium and lithium are expensive, sodium, potassium, rubidium and cesium are suitable for industrial use.

Other catalysts consisting of an oxide composition which falls outside the scope of the above-mentioned empirical formula, for example, which contains cobalt and/or nickel, iron, bismuth, aluminium and/or titanium in an amount or amounts falling outside the scope of the above-mentioned empirical formula, result in a decrease in the percent of yield of acrolein or methacrolein, the percent of conversion of propylene or isobutylene, the percent of selectivity to acrolein or isolutylene and/or the space time yield of acrolein or methacrolein.

In the catalyst usable for the present invention, the component elements are in the form of various types oxides, for example, a simple oxide in which a single element is bonded with oxygen, and a complex oxide in which a plurality of elements are bonded with oxygen, for example, cobalt molybdate, nickel molybdate, iron molybdate, aluminium molybdate, bismuth titanate, bismuth ferrate, bismuth molybdate and bismuth aluminate, or a mixture of the above-mentioned simple oxide and complex oxide.

The catalyst usable for the process of the present invention can be prepared by any conventional methods pertinent for producing a conventional oxide composition catalyst, for instance, an evaporation method, impregnation method and co-precipitation method. Usually, the catalyst can be prepared by providing an aqueous mixture containing the respective element-containing compounds which are starting materials. The starting materials may be in the form of a simple oxide, hydroxide or salt of the respective element, or a complex compound of two or more of the elements with oxygen, or a mixture of two or more of the above-mentioned simple oxide, hydroxide and salt, and the complex compound. However, it is preferable that the starting materials be soluble in water. The water-soluble starting materials are effective for producing an excellent catalyst in which the catalyst components are uniformly mixed and which has a uniform quality and an excellent reproducibility.

The aqueous mixture may be prepared, for example, by suspending a predetermined amount of a titanium compound, for example, titanium dioxide in an aqueous solution of a predetermined amount of a molybdenum compound, for instance, ammonium molybdate, and then, by mixing the resultant aqueous solution-suspension with a solution of predetermined amounts of compounds, for example, nitrates, of cobalt and/or nickel, bismuth, iron, aluminium and, optionally, alkali metal in water or nitric acid. The aqueous mixture of the respective starting materials is converted into a dry mixture by means of evaporation at an elevated temperature. The dry mixture is calcined at an elevated temperature of from 350° to 700° C., preferably, from 400° to 650° C., for 0.5 to 20 hours, preferably, 5 to 7 hours, to convert it into catalyst of the above-mentioned empirical formula.

The molybdenum-containing compound may be molybdic acid, ammonium molybdate or molybdenum trioxide. The cobalt-containing compound may be cobalt nitrate, cobalt carbonate, cobalt (II) or (III) oxide, tricobalt tetroxide, cobalt (II) or (III) hydroxide, cobalt oxalate, or cobalt chloride. The nickel-containing compound may be nickel nitrate, nickel carbonate, nickel (II) or (III) oxide, trinickel tetroxide, nickel (II) or (III) hydroxide, nickel acetate, nickel oxalate or nickel chloride. The iron-containing compound may be ferrous or ferric nitrate, ferrous or ferric oxide, ferrous or ferric hydroxide, ferrous or ferric carbonate or ferrous or ferric chloride. The bismuth-containing compound may be bismuth nitrate, bismuth trioxide, bismuth dichloride, bismuth trichloride, bismuth pentoxide, bismuth oxynitrate or bismuth hydroxide. The aluminium-containing compound may be aluminium nitrate, aluminium hydroxide, or aluminium chloride. The titanium-containing compound may be titanium dioxide or titanium trichloride. The alkali metal-containing compound may be a nitrate, carbonate, chloride or hydroxide of the alkali metal.

The catalyst usable for the present invention may be used alone or in combination with a carrier. The carrier may be selected from any of the conventional ones which are usable for the conventional catalyst for the oxidation process of propylene or isobutylene, for instance, silica, diatomaceous earth and silicon carbide. The amount of the carrier is not limited to a special range or amount as long as the resultant catalyst is effective for the process of the present invention. Usually, it is preferable that the amount of the carrier be in a range of from 0.05 to 0.7 g per g of the oxide composition.

The size and shape of the catalyst are not limited a special size and shape. That is, the carrier can be screened into a desired size and can be formed into a desired form, for instance, powder, grains, pellets, or tablets having a desired crushing strength, depending upon the purpose and condition under which the catalyst is used.

The above-mentioned type of catalyst exhibits an excellent crushing strength and is effective for producing acrolein or methacrolein in a high percent of yield thereof. Accordingly, the catalyst causes the process of the present invention to be industrially more advantageous than the conventional processes.

The reaction feed to be fed into the process of the present invention is prepared by mixing a propylene- or isobutylene-containing gas and a molecular oxygen-containing gas. It is not necessary that the propylene- or isobutylene-containing gas consist of pure propylene or isobutylene. That is, the propylene- or isobutylene-containing gas may contain a small amount of saturated hydrocarbons which are not active under the conditions under which the catalytic oxidation reaction is carried out, for instance, methane, ethane, propane, n-butane and isobutane. The amount of the saturated hydrocarbon compounds is preferably 0.5 mole or less, preferably, 0.1 mole or less, per mole of propylene or isobutylene in the reaction feed. It is desirable that unsaturated hydrocarbons other than propylene or isobutylene, for example, n-butylene and acetylene, should not be present in the reaction feed.

The concentration of the propylene or isobutylene in the reaction feed may be in a range of from 2 to 10% by volume.

It is not always required that the molecular oxygen-containing gas consist of highly pure oxygen alone. Usually, the molecular oxygen-containing gas contains, in addition to the molecular oxygen, an inert diluent gas, for example, steam, nitrogen or carbon dioxide, which are non-reactive under the conditions under which the catalytic oxidation reaction is carried out. The amount of the inert diluent gas is preferably 0.5 mole or more per mole of propylene or isobutylene. The steam is effective not only for accelerating the catalytic oxidation of propylene or isobutylene and for increasing the percent of selectivity to acrolein or methacrolein, but also, for enhancing the durability of the catalytic activity of the catalyst (catalyst life). Accordingly, it is preferable to carry out the catalytic oxidation reaction in the presence of the steam.

The catalytic oxidation reaction in the process of the present invention is usually carried out at a temperature of from 200° to 500° C., preferably, from 250° to 400° C. The oxidation reaction is usually carried out under atmospheric pressure. However, the oxidation reaction can be carried out under a slightly elevated pressure or a slightly reduced pressure. The contact time of the reaction feed with the catalyst may be in a range of from 0.2 to 7 seconds, preferably, from 0.5 to 4 seconds, more preferably, about 2 seconds.

The oxidation reaction in the process of the present invention may be carried out in any type of reactors, for example, fixed bed reactors, moving bed reactors and fluidized bed reactors. In the case where a fludized bed reactor is used for the oxidation reaction, it is preferable that the particles of catalyst have a size of from 30 to 100 microns.

The specific examples set forth below will serve to more fully explain the practice of the process of the present invention. However, it should be understood that the examples are only illustrative and should be in no way interpreted as limiting the scope of the present invention.

In the examples, the percent of conversion of propylene or isobutylene, percent of selectivity to acrolein or methacrolein, percent of yield of acrolein or methacrolein, and space time yield of acrolein or methacrolein are respectively calculated in accordance with the following equations.

Percent of conversion of propylene or isobutylene =
$$\frac{X_1 - X_2}{X_1} \times 100$$

Percent of selectivity to acrolein or methacrolein =
$$\frac{Y}{X_1 - X_2} \times 100$$

Percent of yield of acrolein or methacrolein =
$$\frac{Y}{X_1} \times 100 \text{ and}$$

Space time yield of acrolein or methacrolein in g/l of catalyst.hr = W/Z
wherein
$X_1$: a molar amount of propylene or isobutylene fed;
$X_2$: a molar amount of propylene or isobutylene not consumed;
Y: a molar amount of the resulting acrolein or methacrolein;
W: an amount in gram of the resulting acrolein or methacrolein produced in one hour, and;
Z: an amount in liter of a catalyst used.

Also, the percent of yield of acrylic acid or methacrylic acid = A/X$_1$ × 100, wherein A: a molar amount of the resultant acrylic acid or methacrylic acid.

The crushing strength of the catalyst was determined by the following method.

A catalyst which had been shaped in a tablet (5 mm in diameter and 5 mm in height) was placed on a testing plate and compressed by using a Kiya-type pressing tester until the tablet was crushed. The value of the compressive load in Kg under which the tablet was crushed was measured. The above-mentioned measuring operations were carried out on 50 tablets. The strength necessary to crush the catalyst (crushing strength) was represented by an average value calculated from the results of 50 measurements.

EXAMPLE 1

An aqueous solution was prepared by dissolving 176.6 g of ammonium molybdate [(NH$_4$)$_6$Mo$_7$O$_{24}$.4H$_2$O] in 200 ml of hot water at a temperature of 80° C. Then, 40.0 g of titanium dioxide [TiO$_2$] was suspended in the aqueous solution while stirring. The resulting aqueous suspension solution was mixed, while stirring, with an aqueous solution of 145.5 g of cobalt nitrate [Co(NO$_3$)$_2$.6H$_2$O], 58.2 g of nickel nitrate [Ni(NO$_3$)$_2$.6H$_2$O], 80.8 g of ferric nitrate [Fe(NO$_3$)$_3$.9H$_2$O], 75.0 g of aluminium nitrate [Al(NO$_3$)$_3$.9H$_2$O] and 0.51 g of potassium nitrate [KNO$_3$] in 250 ml of hot water at a temperature of 80° C. and a solution of 9.69 g of bismuth nitrate [Bi(NO$_3$)$_3$.5H$_2$O] in 10 ml of a 15% aqueous solution of nitric acid, to provide an aqueous slurry mixture. The aqueous slurry was placed in an evaporating dish and evaporated to convert it into a solid. The solid was dried at a temperature of 200° C. for 5 hours. The resultant dry solid mixture was pulverized, and then shaped into a number of tablets having a diameter of 5 mm and a height of 5 mm by using a tablet-making machine. The tablets were calcined at a temperature of 550° C. for 5 hours to produce a catalyst. The empirical formula of the oxide composition of the catalyst, except for oxygen, was as follows $Mo_{10}Co_5Ni_2Fe_2Bi_{0.2}Al_2Ti_5K_{0.05}$ A U-shaped glass tube having an inside diameter of 8 mm was charged with 8 ml of the above-prepared catalyst tablets. A reaction feed consisting of propylene, air and steam in a molar ratio of 1:10:4 was flowed at a flow rate of 282 ml/min through the layer of the catalyst tablets in the U-shaped tube. The contact of the reaction feed with the catalyst tablets was carried out at a temperature of 350° C. for 1.7 seconds. The results of the catalytic oxidation was detected after two hours had elapsed from the start of the reaction. The results are indicated in Table 1. In this oxidation, acrolein was produced in a space time yield of 323.0 g/l hr.

The catalyst tablets exhibited an excellent crushing strength of 8.0 Kg per tablet.

EXAMPLES 2 through 10

In each of the Examples 2 through 10, the same procedures as those described in Example 1 were carried out, except that the resultant catalyst had a composition as indicated in Table 1. The results of the catalytic reaction in each example are indicated in Table 1.

COMPARATIVE EXAMPLE 1

The same procedures as those described in Example 1 were carried out, except that no titanium dioxide was used. The empirical formula of the resultant comparative catalyst was as follows $Mo_{10}Co_5Ni_2Fe_2Bi_{0.2}Al_2K_{0.05}$ The resultant comparative catalyst tablets exhibited a poor crushing strength of 4.5 Kg/tablet.

The results of the comparative catalytic reaction are indicated in Table 1.

COMPARATIVE EXAMPLE 2

The same procedures as those described in Comparative Example 1 were carried out, except that the tablet-shaping operation was carried out under such a high degree of compression that the resultant tablets exhibited a crushing strength of 8.0 Kg/tablet. The results of the comparative catalytic reaction are indicated in Table 1.

COMPARATIVE EXAMPLES 3 THROUGH 7

In each of the Comparative Examples 3 through 7, the same procedures as those described in Example 1 were carried out, except that the resultant catalyst had the composition indicated in Table 1.

The results of the comparative catalyst reaction in each comparative example are indicated in Table 1.

TABLE 1

| Example No. | Composition (atomic ratio) of catalyst | | | | | | | | Conversion of propylene (%) | Selectivity to acrolein (%) | Yield of acrolein (%) | Yield of acrylic acid (%) |
|---|---|---|---|---|---|---|---|---|---|---|---|---|
| | Mo | Co | Ni | Fe | Bi | Al | Ti | K | | | | |
| Example | | | | | | | | | | | | |
| 1 | 10 | 5 | 2 | 2 | 0.2 | 2 | 5 | 0.05 | 97.6 | 93.7 | 91.5 | 1.7 |
| 2 | 10 | 5 | 2 | 2 | 0.2 | 2 | 3 | 0.05 | 97.8 | 93.2 | 91.1 | 1.9 |
| 3 | 10 | 5 | 2 | 2 | 0.2 | 2 | 10 | 0.05 | 95.0 | 94.0 | 89.3 | 1.5 |
| 4 | 10 | 6 | 3 | 2 | 0.2 | 2 | 5 | 0.05 | 98.1 | 93.0 | 91.2 | 2.0 |
| 5 | 10 | 7 | 0 | 2 | 0.2 | 2 | 5 | 0.05 | 95.7 | 94.1 | 90.0 | 1.6 |
| 6 | 10 | 2 | 5 | 2 | 0.2 | 2 | 5 | 0.05 | 98.3 | 92.2 | 90.6 | 1.9 |
| 7 | 10 | 3 | 4.5 | 2 | 0.2 | 2 | 5 | 0.05 | 98.5 | 91.9 | 90.5 | 2.1 |
| 8 | 10 | 0 | 7 | 2 | 0.2 | 2 | 5 | 0.05 | 94.0 | 94.1 | 88.5 | 2.0 |
| 9 | 10 | 5 | 2 | 3 | 0.2 | 2 | 3 | 0.05 | 97.4 | 93.3 | 90.9 | 1.9 |
| 10 | 10 | 6 | 2 | 3 | 0.2 | 1 | 5 | 0.05 | 99.0 | 92.0 | 91.1 | 2.3 |
| Comparative Example | | | | | | | | | | | | |
| 1 | 10 | 5 | 2 | 2 | 0.2 | 2 | 0 | 0.05 | 98.2 | 83.2 | 81.7 | 3.9 |
| 2 | 10 | 5 | 2 | 2 | 0.2 | 2 | 0 | 0.05 | 90.4 | 80.9 | 73.1 | 4.1 |
| 3 | 10 | 5 | 2 | 2 | 0.2 | 2 | 20 | 0.05 | 81.3 | 92.0 | 74.9 | 1.8 |
| 4 | 10 | 0.5 | 0 | 2 | 0.2 | 2 | 5 | 0.05 | 68.1 | 70.4 | 47.9 | 3.8 |
| 5 | 10 | 6 | 3 | 2 | 0.2 | 0 | 5 | 0.05 | 97.5 | 79.7 | 77.7 | 4.5 |

TABLE 1-continued

| Example No. | Composition (atomic ratio) of catalyst | | | | | | | Conversion of propylene (%) | Selectivity to acrolein (%) | Yield of acrolein (%) | Yield of acrylic acid (%) |
|---|---|---|---|---|---|---|---|---|---|---|---|
| | Mo | Co | Ni | Fe | Bi | Al | Ti | K | | | | |
| 6 | 10 | 5 | 3 | 3 | 5 | 15 | 5 | 0.05 | 59.8 | 86.6 | 51.8 | 7.8 |
| 7 | 10 | 1 | 7 | 3 | 0 | 3 | 5 | 0.03 | 47.7 | 50.4 | 24.0 | 3.2 |

EXAMPLE 11

Procedures identical to those mentioned in Example 1 were carried out, except that the calcination was carried out at a temperature of 600° C., the reaction feed contained isobutylene in place of propylene, and the catalytic oxidation reaction was carried out at a temperature of 380° C.

The catalyst tablets exhibited a crush strength of 8.5 Kg/tablet.

The results of the catalytic reaction are indicated in Table 2.

COMPARATIVE EXAMPLE 8

The same procedures as those mentioned in Example 11 were carried out, except that no titanium dioxide was used.

The resultant comparative catalyst tablets exhibited a poor crushing strength of 4.7 Kg/tablet.

The results of the comparative catalytic reaction are indicated in Table 2.

EXAMPLES 12 THROUGH 15

In each of the Examples 12 through 15, the same procedures as those mentioned in Example 1 were carried out, except that no potassium nitrate was used in Example 12, and the potassium nitrate was replaced by sodium nitrate in Example 13, by rubidium nitrate in Example 14, by a mixture of potassium nitrate and cesium nitrate in Example 15, and the resultant catalyst was of the composition indicated in Table 3. Also, the tablet-shaping operation was carried out under such a compressing condition that the resultant tablets exhibited a crushing strength of 8.0 Kg/tablet.

The results of the catalytic reaction in each example are shown in Table 3.

EXAMPLE 16

Procedures identical to those mentioned in Example 1 were carried out, except that the aqueous slurry mixture was admixed with 140 ml of an aqueous solution of 30% by weight of silica sol. The resulting catalyst tablets were composed of 80% by weight of a catalyst of the composition ($Mo_{10}Co_5Ni_2Fe_2Bi_{0.2}Al_2Ti_5K_{0.05}$) and 20% by weight of $SiO_2$.

The results of the catalytic reaction are indicated in Table 3.

TABLE 2

| Example No. | Composition of catalyst | butylene (%) | mathacrylic (%) | mathacrylic (%) | mathacrylic g/l · hr | crylic acid (%) |
|---|---|---|---|---|---|---|
| 11 | * | 98.6 | 85.0 | 83.8 | 370 | 3.0 |
| Comparative Example 8 | ** | 98.9 | 80.4 | 79.5 | 351 | 3.7 |

Note:
*$Mo_{10}Co_5Ni_2Fe_2Bi_{0.2}Al_2Ti_5K_{0.05}$
**$Mo_{10}Co_5Ni_2Fe_2Bi_{0.2}Al_2K_{0.05}$ (Columns: Conversion of isobutylene, Selectivity to mathacrylic, Yield of mathacrylic, Space time Yield of mathacrylic, Yield of mathacrylic acid)

TABLE 3

| Example No. | Composition (atomic ratio) of catalyst | | | | | | | | Conversion of propylene (%) | Selectivity to acrolein (%) | Yield of acrolein (%) | Yield of acrylic acid (%) |
|---|---|---|---|---|---|---|---|---|---|---|---|---|
| | Mo | Co | Ni | Fe | Bi | Al | Ti | Alkali metal | | | | |
| 12 | 10 | 5 | 2 | 2 | 0.2 | 2 | 3 | 0 | 98.5 | 86.5 | 85.2 | 3.6 |
| 13 | 10 | 5 | 2 | 2 | 0.5 | 3 | 3 | Na = 0.05 | 97.7 | 91.4 | 89.3 | 2.1 |
| 14 | 10 | 5 | 3 | 1.5 | 0.5 | 3 | 3 | Rb = 0.04 | 97.0 | 92.8 | 90.0 | 2.0 |
| 15 | 10 | 6 | 2 | 3 | 0.2 | 3 | 3 | K = 0.02, Cs = 0.02 | 97.3 | 92.4 | 89.9 | 2.2 |
| 16 | 10 | 5 | 2 | 2 | 0.2 | 2 | 5 | K = 0.05 | 97.8 | 93.0 | 90.9 | 1.7 |

EXAMPLES 17 THROUGH 23

In each of the Examples 17 through 23, procedures identical to those described in Example 1 were carried out, except that the catalyst had the composition indicated in Table 4.

The results of the catalytic reaction in each example are indicated in Table 4.

TABLE 4

| Example No. | Composition (atomic ratio) of catalyst | | | | | | | | Conversion of propylene (%) | Selectivity to acrolein (%) | Yield of acrolein (%) | Yield of acrylic acid (%) |
|---|---|---|---|---|---|---|---|---|---|---|---|---|
| | Mo | Co | Ni | Fe | Bi | Al | Ti | K | | | | |
| 17 | 10 | 5 | 2 | 2.5 | 0.01 | 1 | 3 | 0.05 | 95.8 | 90.7 | 86.9 | 2.3 |
| 18 | 10 | 5 | 2 | 2.5 | 0.05 | 1 | 3 | 0.05 | 98.4 | 92.5 | 91.0 | 2.1 |
| 19 | 10 | 5 | 2 | 2 | 0.1 | 1 | 3 | 0.05 | 97.0 | 93.2 | 90.4 | 1.9 |
| 20 | 10 | 5 | 2 | 2 | 1 | 1 | 3 | 0.05 | 93.8 | 94.3 | 88.5 | 1.9 |
| 21 | 10 | 6 | 1.5 | 3 | 0.03 | 1.5 | 2 | 0.05 | 96.6 | 91.8 | 88.7 | 2.5 |
| 22 | 10.45 | 7 | 0 | 2.5 | 0.07 | 1 | 1 | 0.06 | 95.5 | 92.8 | 88.6 | 2.3 |
| 23 | 10.45 | 7 | 0 | 2.5 | 0.05 | 1 | 1 | 0.08 | 97.5 | 92.3 | 89.9 | 2.5 |

What we claim is:

1. A process for the catalytic preparation of acrolein or methacrolein, comprising bringing, at a temperature of from 200° to 500° C., a reaction feed containing propylene or isobutylene and molecular oxygen, each in gas phase, into contact with a catalyst consisting essentially of an oxide composition of the empirical formula:

$$Mo_aCo_bNi_cFe_dBi_eAl_fTi_gA_hO_i$$

wherein A represents at least one alkali metal atom; the subscripts a, b, c, d, e, f, g and h respectively denote the numbers of the respective atoms of the elements, the ratio a:b:c:d:e:f:g:h being in a range of 10:0 to 10:0 to 10:0.1 to 5:0.001 to 3:0.05 to 10:1 to 15:0 to 4 and the ratio a:(b+c) being in a range of 10:1 to 10, and; the subscript i represents the number of oxygen atoms which satisfies the average valency of the elements, the ratio a:i being in a range of 10:33.2 to 99.

2. A process as claimed in claim 1, wherein said alkali metal is selected from the group consisting of sodium, potassium, rubidium and cesium.

3. A process as claimed in claim 1, wherein the ratio a:b:c:d:e:f:g:h is in a range of 10:0 to 10:0 to 10:1 to 3:0.05:2:1 to 5:3 to 10:0.065 to 0.5, and the ratio a:(b+c) being in a range of 10:1 to 10.

4. A process as claimed in claim 1, wherein said catalyst is prepared by calcining a dry solid mixture containing a molybdenum-containing compound, a cobalt-containing compound, a nickel-containing compound, an iron-containing compound, a bismuth-containing compound, an aluminum-containing compound, a titanium compound and at least one-alkali metal-containing compound, at a temperature of from 350° to 700° C. in an oxygen-containing atmosphere.

5. A process as claimed in claim 4, wherein said calcining operation is carried out for from 0.5 to 20 hours.

6. A process as claimed in claim 1, wherein said catalyst is borne on a carrier consisting of at least one member selected from silica, diatomaceous earth and silicon carbide.

7. A process as claimed in claim 1, wherein the amount of said molecular oxygen in said reaction feed is in a range of 0.8 to 5 moles per mole of propylene or isobutylene.

8. A process as claimed in claim 1, wherein said reaction feed contains, in addition to said molecular oxygen and propylene or isobutylene, an inert diluent gas selected from the group consisting of steam, nitrogen gas and carbon dioxide gas, in an amount of 0.5 moles or more per mole of propylene or isobutylene.

9. A process as claimed in claim 1, wherein said contacting operation is carried out at a temperature of from 250° to 400° C.

10. A process as claimed in claim 1, wherein said contacting operation is carried out for from 0.2 to 7 seconds.

11. A process as claimed in claim 1, wherein the concentration of said propylene or isobutylene in said reaction feed is in a range of from 2 to 10% by volume.

* * * * *

UNITED STATES PATENT AND TRADEMARK OFFICE
CERTIFICATE OF CORRECTION

PATENT NO. : 4,267,385
DATED : May 12, 1981
INVENTOR(S) : Sumio Umemura et al.

It is certified that error appears in the above—identified patent and that said Letters Patent is hereby corrected as shown below:

Column 3, line 34, change "respresents" to --represents--.

Column 5, line 34, after "limited" insert --to--.

TABLE 2, column 9, in the title, "mathacrylic" (4 instances) should read --methacrylic--.

Signed and Sealed this

Thirteenth Day of October 1981

[SEAL]

Attest:

GERALD J. MOSSINGHOFF

*Attesting Officer*     *Commissioner of Patents and Trademarks*

UNITED STATES PATENT AND TRADEMARK OFFICE
CERTIFICATE OF CORRECTION

PATENT NO. : 4,267,385
DATED : May 12, 1981
INVENTOR(S) : Sumio Umemura, et al

It is certified that error appears in the above—identified patent and that said Letters Patent is hereby corrected as shown below:

In the title page, under item [75]: Please insert the name of the fourth inventor, Masao Tsuruoka of Ube, Japan.

Signed and Sealed this

First Day of December 1981

[SEAL]

Attest:

GERALD J. MOSSINGHOFF

Attesting Officer    Commissioner of Patents and Trademarks